(12) United States Patent
Pettersson et al.

(10) Patent No.: US 6,845,261 B2
(45) Date of Patent: Jan. 18, 2005

(54) SYSTEM FOR CORRELATION OF MR IMAGES WITH PHYSIOLOGICAL DATA

(75) Inventors: Bo Pettersson, Wauwatosa, WI (US); Robert Holden Haworth, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 624 days.

(21) Appl. No.: 09/840,361

(22) Filed: Apr. 23, 2001

(65) Prior Publication Data

US 2002/0156367 A1 Oct. 24, 2002

(51) Int. Cl.⁷ ................................................. A61B 3/16
(52) U.S. Cl. ........................................................ 600/413
(58) Field of Search ............................... 600/413, 410, 600/407, 436, 417; 324/307, 308, 309; 436/173

(56) References Cited

U.S. PATENT DOCUMENTS

| | | | | |
|---|---|---|---|---|
| 4,245,646 A | * | 1/1981 | Ionnou et al. | 600/407 |
| 5,329,925 A | * | 7/1994 | NessAiver | 600/413 |
| 5,435,303 A | * | 7/1995 | Bernstein et al. | 600/413 |
| 5,781,010 A | * | 7/1998 | Kawasaki et al. | 324/309 |
| 6,144,200 A | * | 11/2000 | Epstein et al. | 324/306 |
| 6,275,721 B1 | * | 8/2001 | Darrow et al. | 600/410 |
| 6,330,467 B1 | * | 12/2001 | Creighton et al. | 600/407 |
| 6,522,909 B1 | * | 2/2003 | Garibaldi et al. | 600/424 |

* cited by examiner

Primary Examiner—Daniel Robinson
(74) Attorney, Agent, or Firm—Joseph S. Heino; Patrick M. Bergin; Q. Todd Dickinson

(57) ABSTRACT

An MR system correlates MR images with acquired physiological data. MR image data and physiological data is acquired through two independent pipelines. Both pipelines range from analog to digital conversion to image or data display. The pipelines are synchronized by triggers calculated from data contained in the physiological pipeline which are then used to trigger the acquisition of data in the MR image pipeline. Another embodiment includes time synchronization of a distributed acquisition and processing system having the ability to correlate physiological and MR data using a common time base and the ability to selectively store physiological data. Simplified network time protocol is used to synchronize timers and a separate data conduit is used for sending physiological data to the data store process. This supports different modes of synchronization between acquisition and the physiological signal.

17 Claims, 4 Drawing Sheets

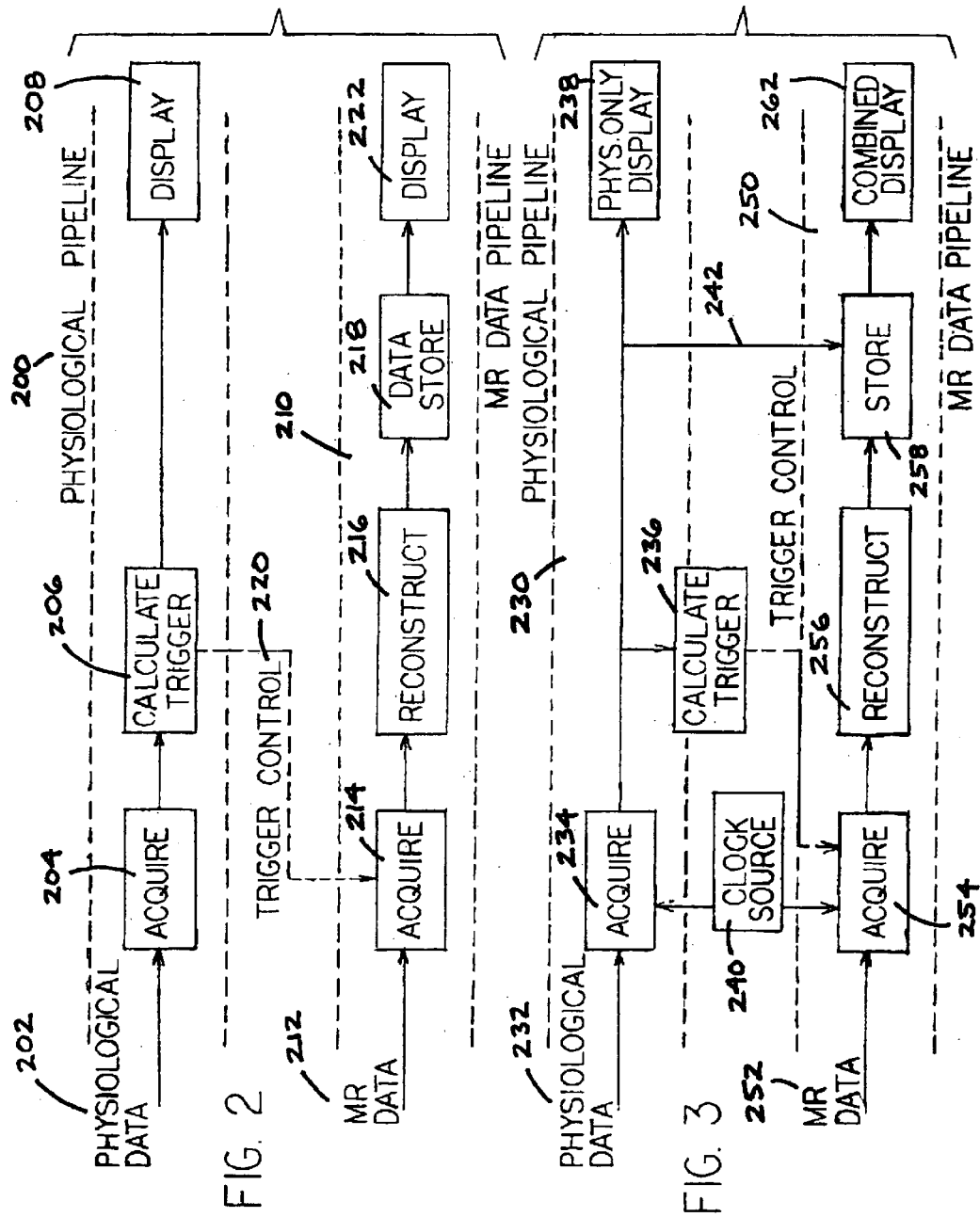

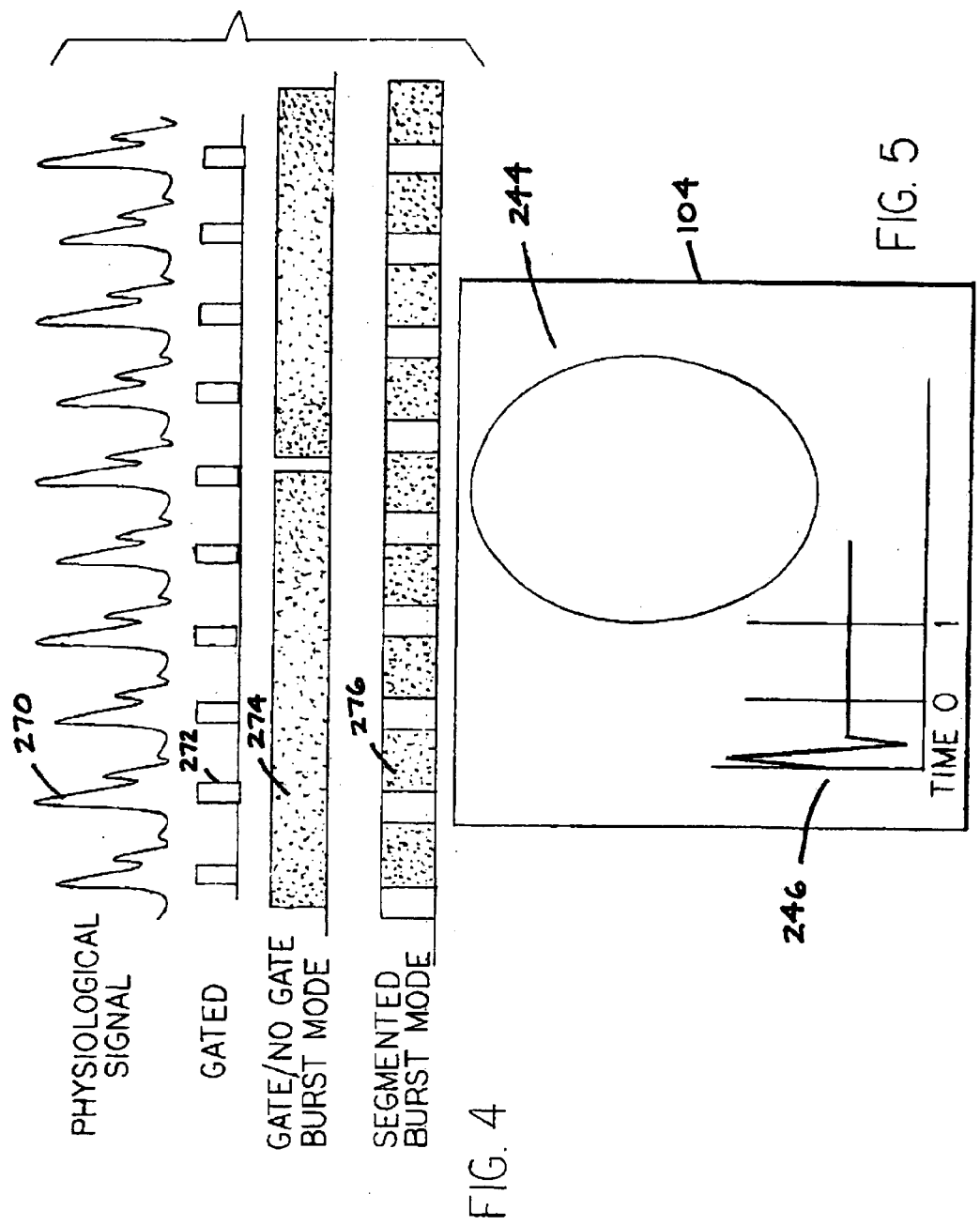

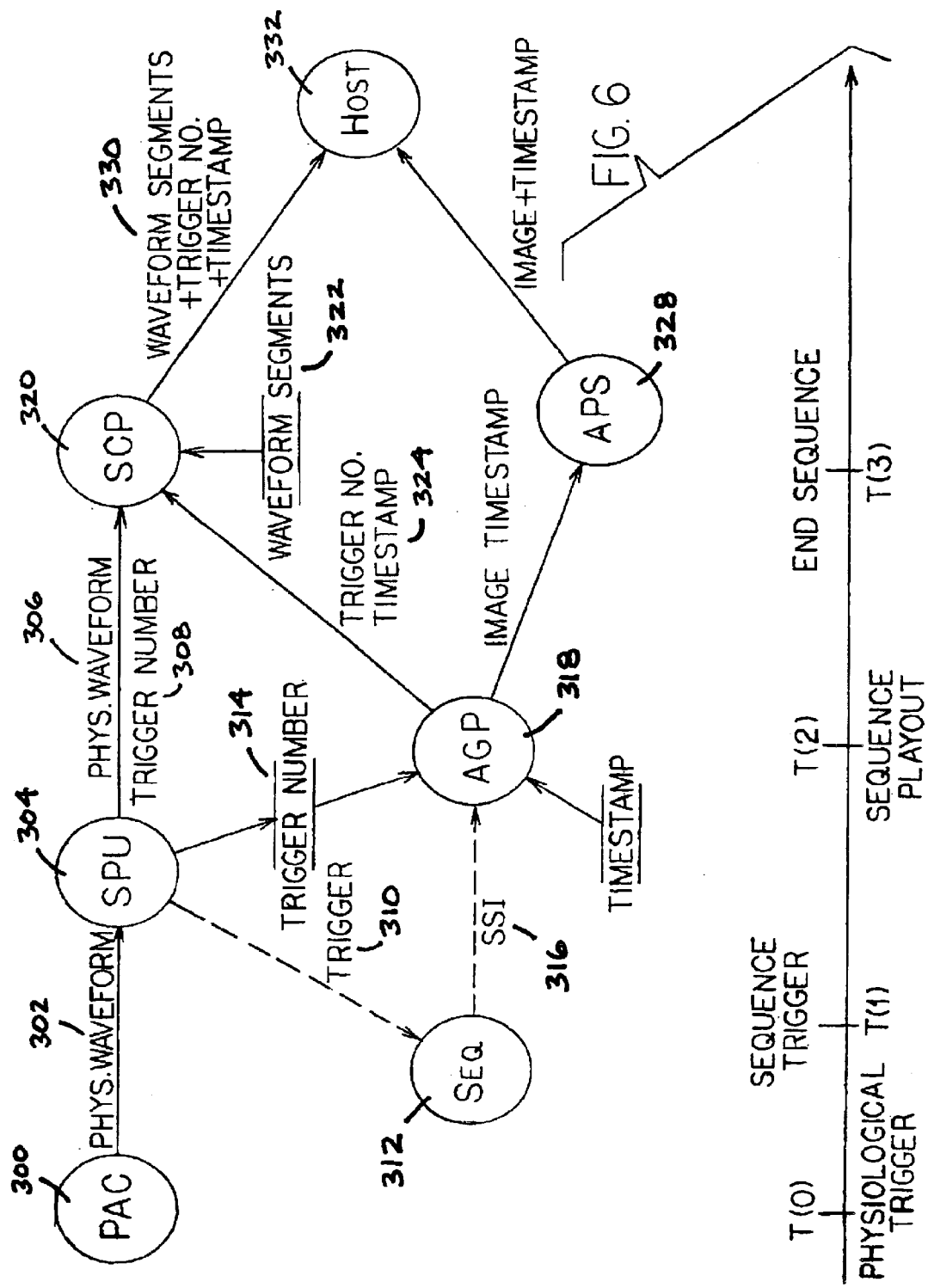

ns (excitation field $B_1$) which is in the x-y plane and which is near the Larmor frequency, the net aligned moment $M_z$, may be rotated, or "tipped," into the x-y plane to produce a net transverse magnetic moment Mt. A signal is emitted by the excited spins after the excitation signal $B_1$ is terminated. This signal may be received and processed to form an image.

SYSTEM FOR CORRELATION OF MR IMAGES WITH PHYSIOLOGICAL DATA

BACKGROUND OF THE INVENTION

The field of the invention is magnetic resonance ("MR") imaging methods and systems. More particularly, the invention relates to an MR system which correlates MR images with acquired physiological data.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment $M_z$, may be rotated, or "tipped," into the x-y plane to produce a net transverse magnetic moment Mt. A signal is emitted by the excited spins after the excitation signal $B_1$ is terminated. This signal may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received signals are digitized and processed to reconstruct the image using one of many well-known reconstruction techniques.

A magnetic resonance imaging ("MRI") system which processes and reconstructs such signals may be offered with a range of polarizing magnetic strengths and configurations. The MRI system may also be offered with a range of different optional features such as magnetic resonance angiography ("MRA"), cardiac imaging and functional magnetic resonance imaging ("fMRI"). Despite such differences, all MRI systems include an operator interface which enables a particular image acquisition to be prescribed, a data acquisition apparatus which uses the MR imaging modality to acquire data from a subject, an image reconstruction processor for reconstructing an image using acquired data, storage apparatus for storing images and associated patient information and an image display apparatus. A specific hardware component is provided to carry out each of these functions and software is designed and written for each hardware configuration.

With new real time clinical applications, the importance of being able to correlate physiological data such as electrocardiogram signals ("ECG"), electroencephalogram signals ("EEG"), evoked potential signals or sensory excitation signals used in functional imaging studies to MRI images has been recognized. In the area of cardiac imaging, there is also a need to correlate an MRI image to the specific part of the cardiac cycle that the image came from so that a physician can determine whether appropriate heart function is occurring. Currently, there are no MRI systems with built-in hardware and software to provide this visual correlation. Visual correlation between physiological signals and MR images is expected to enhance clinical utility of the MRI scanner.

BRIEF SUMMARY OF THE INVENTION

In an illustrative embodiment of the invention, MR image data and physiological data is acquired through two independent pipelines. Both pipelines range from analog to digital conversion to image or data display. The pipelines are synchronized, but only in a limited fashion. That is, triggers (e.g., heartbeats) calculated from data contained in the physiological pipeline could be used to trigger the acquisition of data in the MR image pipeline.

Another embodiment provides hardware and software to fully correlate the physiological data with the MR image data. The key components for doing this include time synchronization of a distributed acquisition and processing system with up to 200 microseconds resolution, ability to correlate physiological and MR data using this common time base, and ability to selectively store physiological data. This embodiment uses simplified network time protocol ("SNTP") to synchronize timers across the platform and has a separate data conduit for sending physiological data to the data store process. This architecture also supports different modes of synchronization between acquisition and the physiological signal.

Other principal features and advantages of the present invention will become apparent to those skilled in the art upon review of the following drawings, the detailed description and the appended claims.

BRIEF DESCRIPTION OF THE DRAWINGS

FIG. 2 is a block diagram which abstractly represents the acquisition of physiological data and MR data in one embodiment of the invention.

FIG. 3 is a block diagram which abstractly represents the acquisition of physiological data and MR data in another embodiment of the invention.

FIG. 4 is a graphic representation of three different modes of synchronization between acquisition and physiological signals.

FIG. 5 is illustrates a typical post-acquisition image display as viewed by the MRI operator.

FIG. 6 is a block diagram which shows detailed implementation of this invention in the data acquisition component of the MR scanner.

DETAILED DESCRIPTION OF THE INVENTION

Figure 1:
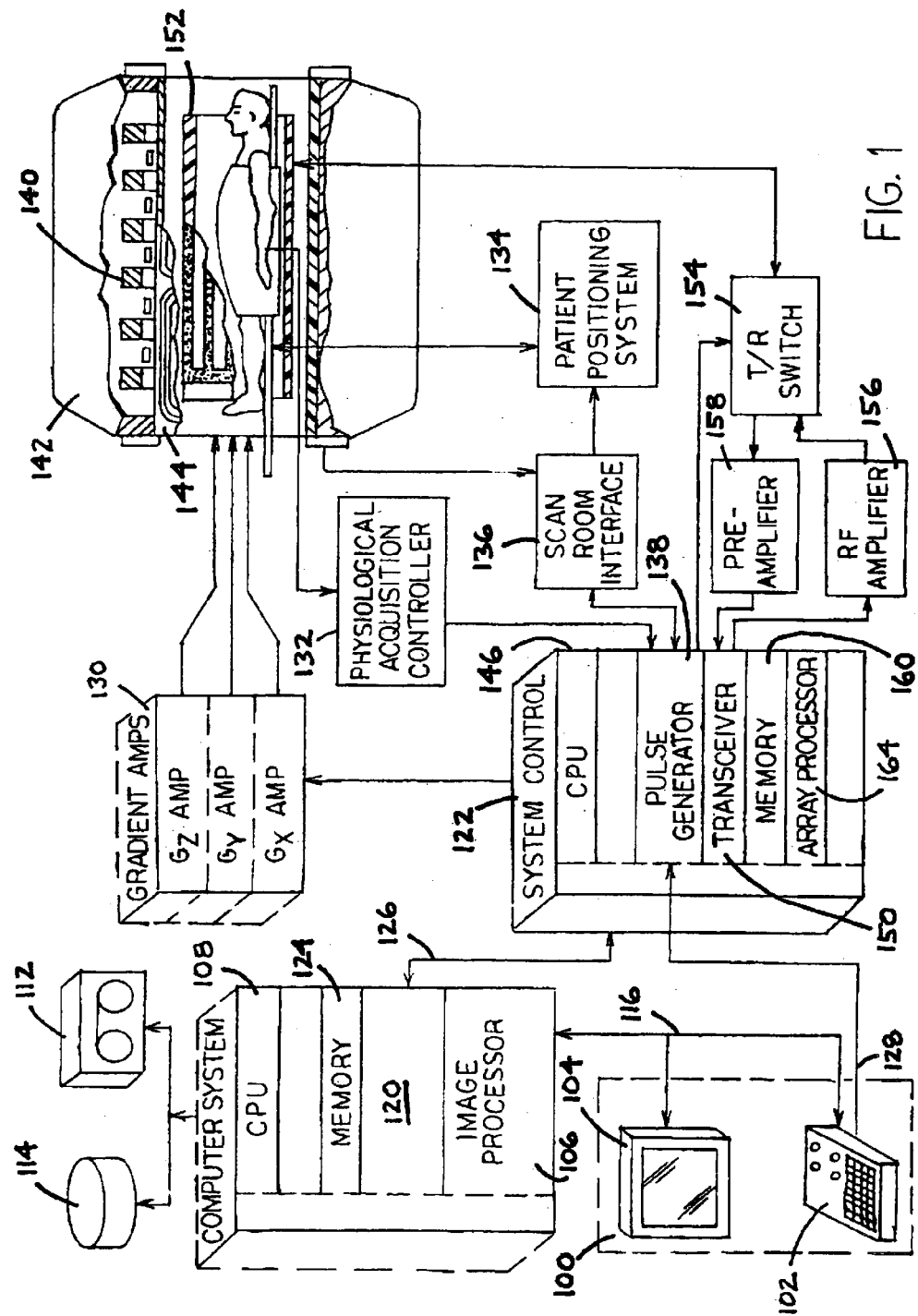
FIG. 1 is a block diagram of an MR imaging system, which employs the present invention.

Referring now to the drawings, wherein like numerals represent like elements throughout, FIG. 1 shows the major components of a preferred MRI system, which incorporates the present invention. The operation of the system is controlled from an operator console 100, which includes a keyboard and control panel 102 and a display 104. The console 100 communicates through a link 116 with a separate computer system 120 that enables an operator to control the production and display of images on the screen 104. The computer system 120 includes a number of modules, which communicate with each other through a backplane. These include an image processor module 106, a central processing unit ("CPU") module 108 and a memory module 124 known in the art as a frame buffer for storing image data arrays. The computer system 120 is linked to a disk storage 114 and a tape drive 112 for storage of image data and programs, and it communicates with a separate system control 122 through a high speed serial link 126.

The system control 122 includes a set of modules connected together by a backplane. These include a CPU module 146 and a pulse generator module 138, which connects to the operator console 100 through a serial link 128. It is through this link 128 that the system control 122 receives commands from the operator, which indicate the scan sequence that is to be performed. The pulse generator module 138 operates the system components to carry out the desired scan sequence. It produces data, which indicates the timing, strength and shape of the RF pulses, which are to be produced, and the timing of and length of the data acquisition window. The pulse generator module 138 connects to a set of gradient amplifiers 130, to indicate the timing and shape of the gradient pulses to be produced during the scan. The pulse generator module 138 also receives patient data from a physiological acquisition controller 132 that receives signals from a number of different sensors connected to the patient, such as ECG signals from electrodes or respiratory signals from a bellow. And finally, the pulse generator module 138 connects to a scan room interface circuit 136, which receives signals from various sensors associated with the condition of a patient and the magnet system. It is also through the scan room interface circuit 136 that a patient positioning system 134 receives commands to move the patient to a desired position for the scan.

The gradient waveforms produced by the pulse generator module 138 are applied to a gradient amplifier system 130 comprised of $G_x$, $G_y$ and $G_z$, amplifiers. Each gradient amplifier excites a corresponding gradient coil in an assembly generally designated 144 to produce the magnetic field gradients used for position encoding acquired signals. The gradient coil assembly 144 forms part of a magnet assembly 142, which includes a polarizing magnet 140 and a whole-body RF coil 152. A transceiver module 150 in the system control 122 produces pulses, which are amplified by an RF amplifier 156 and coupled to the RF coil 152 by a transmit/receive switch 154. The resulting signals radiated by the excited nuclei in the patient may be sensed by the same RF coil 152 and coupled through the transmit/receive switch 154 to a preamplifier 158. The amplified MR signals are demodulated, filtered, and digitized in the receiver section of the transceiver 150. The transmit/receive switch 154 is controlled by a signal from the pulse generator module 138 to electrically connect the RF amplifier 156 to the coil 152 during the transmit mode and to connect the preamplifier 158 during the receive mode. The transmit/receive switch 154 also enables a separate RF coil) for example, a head coil or surface coil) to be used in either the transmit or receive mode.

The MR signals picked up by the RF coil 152 are digitized by the transceiver module 150 and transferred to a memory module 160 in the system control 122. When the scan is completed and an entire array of data has been acquired in the memory module 160, an array processor 164 operates to Fourier transform the data into an array of image data. This image data is conveyed through the link 126 to the computer system 120 where it is stored in the disk memory 114. In response to commands received from the operator console 100, this image data may be archived on the tape drive 112, or it may be further processed by the image processor 106 and conveyed to the operator console 100 and presented on the display 104.

The "legacy" MR scanner hereinafter refers to DAQ88, the data acquisition component of a current MR scanner. In the legacy MR scanner, image data 212 and physiological data 202 is acquired through two independent pipelines 200, 210. The first pipeline 200 is the physiological pipeline 200 through which physiological data 202 is acquired 204. A trigger 270, consisting of a physiological event, is calculated 206 and a display 104, 208 of that physiological data 202 is made visually for use by the operator. See FIGS. 2 and 5. The second pipeline 210 is the MR data pipeline 210 which includes the acquisition 214 of MR data 212, the reconstruction 216 of that acquired data, the storage 218 of that data and an MR display 222. These two pipelines 200, 210 are only synchronized in a limited fashion. The triggers calculated 206 from data 202 contained in the physiological pipeline 200 are used 220 to trigger acquisition 214 of data 212 in the image, or MR data, pipeline 210. However, for posterity, no record of this relationship is created or maintained.

In an alternative embodiment of this invention, a multi-generational DAQ ("MGD") provides hardware and software to fully correlate the physiological data 232 with the MR image data 252 through the two independent pipelines 230, 250. The key components for doing this include time synchronization 240 of a distributed acquisition 234, 254 and processing system with up to 200 microseconds resolution, the ability to correlate physiological data 232 and MR data 252 using this common time base 240, and the ability to selectively store 258 physiological data 232. MGD uses SNTP to synchronize timers 240 across the platform and has a separate data conduit 242 for sending physiological data 232 to the data store 258 process. The physiological data pipeline 230 also includes trigger calculation 236 and visual display 238. The MR data pipeline 250 includes the reconstruction 256 of acquired data 252 and a combined MR display 262. In abstract terms, this architecture appears as shown in FIG. 3.

The MGD architecture supports three different modes of synchronization between acquisition and physiological signals. The three different conditions can be represented as shown in FIG. 4. A physiological signal 270, such as a heart beat, serves as the trigger. The "gated" mode 272 of synchronization is synchronous with this physiological signal or event 270. Alternatively, "gate/no gate" 274 or "segmented burst" 276 modes may be started by the physiological event 270, but, thereafter, are free running and not synchronous. In this mode, physiological data continues to be acquired. The method and system of the present invention consists of acquiring 234, 254 simultaneously a physiological signal 232 and a set of MR image 252 acquisitions. See FIG. 3. These acquisitions 234, 254 can be gated to some point in the physiological wave form or could be performed completely asynchronous with respect to the physiological wave form. It is also possible that a burst of images acquired over a large physiological signal interval can be considered. Similarly, images can be associated with different segments of a somewhat repetitive physiological signal 270.

The detailed implementation of this invention in the MGD scanner is illustrated in FIG. 6. The processing of the MRI system and method of the present invention is as follows. The signal processing unit ("SPU") 304, or digital signal processor ("DSP"), receives unfiltered physiological data 302 from the physiological acquisition controller ("PAC") 300.

For gated scans, the SPU 304 identifies the triggers 310 and, if the triggers 310 meet the specific criteria, triggers the sequencers 312. The sequencers 312 are the processing components that play out RF and gradient wave forms. The SPU 304 also triggers blockout processing in which triggers 310 (such as heart beats) are only accepted in certain hardware states. A start sequence interrupt ("SSI") 316, which is an event that starts the playout of a sequence (RF and gradient wave forms) on the application gateway processor ("AGP") 318, which is the main processor to control the MR sequence, is generated as needed. The trigger number 314 from the SPU 304 is read by the AGP 318 and sent 306,308 to the scan control processor ("SCP") 320, the processor that controls external components, as part of the SSI notification 316. This approach is needed since the SPU 304 is not a SNTP capable processor. Meanwhile, the SCP 320 stores wave form segments 322 (from trigger to trigger), such as cardiac wave form segments, together with the trigger number 308, 314 in a double buffer. The segments 322 are sent to the operator interface workstation, or host 332, at regular intervals, tentatively every 250 milliseconds. If the SCP 320 is notified by the AGP 318 that a given segment has been used, then trigger number and associated timestamp information 324 is forwarded 330 to the host 332. The host 332 knows the time order of the images that have been received based on the timestamp from the Recon, the processing system in charge of computing MR images from raw data via AGP 318, and can complete the association since trigger delay and sequence delays are known system and pulse sequence properties.

For scans that are not gated, AGP 318 provides the SCP 320 with the timestamp 324 associated with the original trigger at the beginning of the scan. The common clock will then ensure that the time association between MR data and physiological data does not drift. The relationship can be correctly restored by data store on the host.

The MGD processors, SPU 304, SCP 320, AGP 318, Acquisition Processing System ("APS") 328 and SEQ 312, run off of the same crystal and so are synchronous. The PAC 300, however, is asynchronous and has its own time base. The interface between the PAC 300 and the SPU 304 has been implemented such that the SPU 304 time reference is enforced and cumulative time reference errors cannot grow beyond one millisecond. Thus, burst sequences utilizing one initial trigger, and then running free with respect to cardiac triggers, will not accumulate time errors larger than one millisecond regardless of run time.

Referring to the timeline at the foot of FIG. 6, at time T (0) the PAC 300 detects a physiological trigger. The SPU 304 will trigger the sequencers 312 at T (1) to play out RF and Gradient waveforms. MR data from which a given image is reconstructed is acquired between times T (2) and T (3). The physiological waveform between T (2) and T (3) will be annotated on the MR image.

The resulting image 242, 244 could, post acquisition, be presented to the operator at his or her monitor 104 as shown in FIG. 5. It should be noted that this association is not necessarily done real time. During real time, for example, the MR image 244 and cardiac waveforms 246 could also be displayed separately with no attempt at exact synchronization. Then retrospectively when the scan is stopped, the operator could display previously acquired images 244 that represent the synchronization of the image acquisition event and ECG waveforms 242. In cases where data has been acquired over many heartbeat to heartbeat ("R/R") intervals for a given cardiac phase, for example, this could be represented with either average or typical physiological data for a more practical implementation.

Several benefits and advantages are derived from the invention. With new real time clinical applications, the importance of being able to correlate physiological data such as ECG, EEG, evoked potential signals or sensory excitation signals used in functional imaging studies to MRI images has been recognized. In the area of cardiac imaging, there is also a need to correlate an MRI image to the specific part of the cardiac cycle that the image came from so that a physician can determine whether appropriate heart function is occurring. Visual correlation between physiological signals and MR images is expected to enhance clinical utility of the MRI scanner.

The foregoing description of an embodiment of the invention has been presented for purposes of illustration. It is to be understood that variations in the details of construction, the arrangement and combination of parts, and the types of materials used may be made without departing from the spirit and scope of the invention as defined by the claims appended hereto.

Parts List:
100 operating console
102 control panel
104 display
106 image processor module
108 central processing unit (CPU)
112 tape drive
114 disk storage
116 link
120 computer system
122 system control
124 memory module
126 high speed serial link
128 serial link
130 gradient amplifiers
132 physiological acquisition controller
134 patient positioning system
136 scan room interface circuit
138 pulse generator module
140 polarizing magnet
142 magnet assembly
144 gradient coil assembly
146 CPU module
150 transceiver module
152 RF coil
154 transmit/receive switch
156 RF amplifier
158 preamplifier
160 memory module
164 array processor
200 physiological pipeline
202 physiological data
204 physiological data acquisition
206 calculate trigger
208 visual display of physiological event
210 MR data pipeline
212 MR image data
214 MR data acquisition
216 MR data reconstruction
218 data storage
220 trigger control
222 MR data display
230 physiological pipeline
232 physiological data
234 physiological data acquisition
236 calculate trigger
238 visual display of physiological event
240 time synchronization
242 data conduit
244 MR image display
246 physiological waveform display
250 MR data pipeline
252 MR image data
254 MR data acquisition
256 MR data reconstruction
258 data store
262 combined visual display
270 physiological signal waveform
272 gated mode synchronization
274 gate/no gate burst mode synchronization 276 segmented burst mode synchronization
300 physiological acquisition controller (PAC)
302 physiological waveform
304 signal processing unit (SPU)
306 physiological waveform
308 trigger number
310 triggers
312 sequencer(SEQ)
314 trigger number
316 start sequence interrupt (SSI)
318 application gateway processor (AGP)
320 scan control processor (SCP)
322 wave form segments
324 image timestamp
328 acquisition processing system (APS)
330 trigger and timestamp data
332 host

What is claimed is:

1. A method for correlating MR images with physiological data, the steps comprising:
    providing a physiological data pipeline;
    acquiring physiological data through the physiological data pipeline;
    providing an MR data pipeline;
    utilizing data acquired in the physiological data pipeline to trigger the acquisition of data within the MR data pipeline;
    acquiring MR data through the MR date pipeline;
    providing a visual display; and
    displaying a physiological data and MR data on the same visual display.

2. The method as recited in claim 1 wherein said physiological data acquisition step further comprises the step of acquiring all or part of a physiological waveform.

3. The method as recited in claim 2 wherein said physiological data acquisition step further comprises the step of calculating a trigger from data acquired in the physiological data pipeline.

4. The method as recited in claim 3, further comprising the step of:
    reconstructing MR data within the data pipeline after the MR data acquisition st p.

5. The method as recited in claim 4, further comprising the step of:
    storing MR data within the MR data pipeline after the MR data reconstruction step.

6. A method for correlating MR images with physiological data, the steps comprising:
    providing a physiological data pipeline;
    acquiring physiological data through the physiological data pipeline;
    providing an MR data pipeline;
    providing time synchronization across the physiological data pipeline and the MR data pipeline to trigger the acquisition of data within the MR data pipeline;
    acquiring MR data through an MR data pipeline;
    providing a visual display; and
    displaying physiological data and MR data on the same visual display.

7. The method as recited in claim 6 wherein said physiological data acquisition step further comprises the step of acquiring all or part of a physiological waveform.

8. The method as recited in claim 7 wherein said time synchronization providing step further comprises providing timers and using simplified network time protocol to synchronize said timers.

9. The method as recited in claim 8, further comprising the step of:
    reconstructing MR data within the MR data pipeline after the MR data acquisition step.

10. The method recited in claim 9, further comprising:
    providing a data store process an storing MR data within the MR data pipeline data store process.

11. The method recited in claim 10, further comprising the step of:
    providing a separate data conduit or sending physiological data to the data store process.

12. A system for correlating MR images with physiological data such that a visual display of the physiological data on the MR image is obtained, which comprises:
    a physiological acquisition controller, said physiological acquisition controller including the ability to digitize physiological signals received by it;
    a physiological signal processing unit;
    a an application gateway processor;
    a scan control processor for controlling external components or an MR device said scan control processor further including means for storing physiological waveform segment and said application gateway processor includes means for notifying the can control processor that a given waveform segment has been used as a trigger whereby on associated trigger number and timestamp is forwarded to the operator interface;
    an acquisition processing system; and
    an operator interface.

13. The image correlation system of claim 12 wherein said physiological signal processing unit further comprises means for receiving physiological data from the physiological acquisition controller.

14. The image correlation system of claim 13 wherein said physiological signal processing unit further comprises means for receiving physiological data in the form of a physiological waveform.

15. The image correlation system of claim 14 wherein said physiological signal processing unit further comprises means for providing a trigger for data acquisition, said trigger being readable by the application gateway processor.

16. The image correlation system of claim 15 wherein said application gateway processor further comprises means for providing time synchronization between a physiological waveform chain and an MR image chain.

17. The image correlation system of claim 16 wherein said application gateway processor further comprises means for providing the scan control processor with the timestamp associated with the original trigger.

* * * * *

UNITED STATES PATENT AND TRADEMARK OFFICE
CERTIFICATE OF CORRECTION

PATENT NO. : 6,845,261 B2 Page 1 of 1
DATED : January 18, 2005
INVENTOR(S) : Pettersson et al.

It is certified that error appears in the above-identified patent and that said Letters Patent is hereby corrected as shown below:

Column 7,
Line 29, replace "date" with -- data --.

Column 8,
Line 18, replace "or" with -- for --.
Line 31, replace "or" with -- of --.
Line 34, replace "can" with -- scan --.

Signed and Sealed this

Eleventh Day of October, 2005

JON W. DUDAS
*Director of the United States Patent and Trademark Office*